United States Patent [19]

Lemanski et al.

[11] Patent Number: 5,536,693
[45] Date of Patent: Jul. 16, 1996

[54] PROCESS FOR THE PREPARATION OF VINYL ACETATE CATALYST

[75] Inventors: Michael F. Lemanski, Chester, N.Y.; Christos Paparizos, Willowick, Ohio; Patricia R. Blum, Macedonia, Ohio; Larry M. Cirjak, Burton, Ohio; Marc A. Pepera, Northfield, Ohio

[73] Assignee: The Standard Oil Company, Cleveland, Ohio

[21] Appl. No.: 252,800

[22] Filed: Jun. 2, 1994

[51] Int. Cl.$^6$ .............................. B01J 23/44; B01J 37/08
[52] U.S. Cl. .................. 502/300; 502/245; 502/326; 502/328; 502/330; 502/331; 502/339
[58] Field of Search ....................... 502/245, 300, 502/326, 328, 330, 331, 339

[56] References Cited

U.S. PATENT DOCUMENTS

| | | | |
|---|---|---|---|
| 3,117,990 | 1/1964 | Adachi et al. | 260/498 |
| 3,275,680 | 9/1966 | Holzrichter et al. | 260/497 |
| 3,670,014 | 6/1972 | Fernholz et al. | 260/497 A |
| 3,686,287 | 8/1972 | Knights | 260/497 A |
| 3,743,607 | 7/1973 | Sennewald et al. | 252/430 |
| 3,759,839 | 9/1973 | Fernholz et al. | 252/431 C |
| 3,761,513 | 9/1973 | Sennewald et al. | 260/497 A |
| 3,775,342 | 11/1973 | Kronig et al. | 252/430 |
| 3,939,199 | 2/1976 | Fernholz et al. | 260/469 |
| 3,950,400 | 4/1976 | Fernholz et al. | 260/497 A |
| 3,969,271 | 7/1976 | Lester | 252/430 |
| 4,048,096 | 9/1977 | Bissot | 252/430 |
| 4,087,622 | 5/1978 | Nakamura et al. | 560/245 |
| 4,188,490 | 2/1980 | Hinnenkamp et al. | 560/245 |
| 4,517,377 | 5/1985 | Isshiki et al. | 560/261 |
| 4,677,084 | 6/1987 | Bergna | 502/8 |
| 4,933,204 | 6/1990 | Warren, Jr. et al. | 427/53.1 |
| 4,978,778 | 12/1990 | Isshiki et al. | 560/261 |
| 5,051,394 | 9/1991 | Haruta et al. | 502/324 |
| 5,179,056 | 1/1993 | Bartley | 502/170 |
| 5,179,057 | 1/1993 | Bartley | 502/170 |
| 5,185,308 | 2/1993 | Bartley et al. | 502/170 |
| 5,225,388 | 7/1993 | Wunder et al. | 502/170 |
| 5,250,487 | 10/1993 | Wirtz et al. | 560/243 |
| 5,292,931 | 3/1994 | Wirtz et al. | 560/245 |
| 5,314,858 | 5/1994 | Colling | 502/330 |
| 5,336,802 | 8/1994 | Smith et al. | 560/245 |

FOREIGN PATENT DOCUMENTS

| | | |
|---|---|---|
| 0519435 | 12/1992 | European Pat. Off. . |
| 687990 | 12/1968 | South Africa . |
| 1266624 | 3/1972 | United Kingdom . |
| 1266623 | 3/1972 | United Kingdom . |
| 1283737 | 8/1972 | United Kingdom . |
| 1333449 | 10/1973 | United Kingdom . |
| 9204976 | 4/1992 | WIPO . |

OTHER PUBLICATIONS

T. Kawaguchi et al., Applied Catalysis, 36 (1988) 67–79. (month unknown).
T. Kawaguchi et al., *Applied Catalysis*, 32 (1987) 23–36. (month unknown).
T. Kawaguchi et al., J. Chem. Tech. Biotechnol., 42 (1988) 113–127. (month unknown).

Primary Examiner—Diana Dudash
Assistant Examiner—Timothy H. Meeks
Attorney, Agent, or Firm—Michael F. Esposito; David J. Untener

[57] ABSTRACT

A process of producing a fluid bed oxacylation catalyst for olefins and diolefins having the following formula Pd-M-A where M=Au, Cd, Bi, Cu, Mn, Fe, Co, Ce, U and mixtures thereof, A=an alkali metal or mixture thereof, and M is present in the range of from 0 to 5 wt %, comprising milling a fixed bed oxacylation catalyst precursor comprising Pd-M on a fixed support with a fluid bed catalyst aqueous binder material to form a uniform aqueous slurry, drying the aqueous slurry to remove the water to form microspheroidal particles of solid fluid bed catalyst precursor, impregnating the microspheroidal particles with a solution of alkali metal salt to form the fluid bed catalyst. The catalyst is particularly useful in the manufacture of vinyl acetate from ethylene, acetic acid and oxygen.

15 Claims, No Drawings

PROCESS FOR THE PREPARATION OF VINYL ACETATE CATALYST

The present invention relates to a process of producing palladium-alkali or palladium/promoter metal/alkali metal catalysts useful in the oxacylation of olefins or diolefins. In particular, effecting the production of vinyl acetate from ethylene, acetic acid and an oxygen containing gas. More particular, the present invention relates to the process of producing palladium-gold-potassium fluid bed catalyst useful in the manufacture of vinyl acetate.

The production of vinyl acetate by reacting ethylene, acetic acid and oxygen together in the gas-phase in the presence of a catalyst containing palladium, gold and an alkali metal acetate promoter is known. The catalyst components are typically supported on a porous carrier material such as silica or alumina.

In early examples of these catalysts, both the palladium and gold were distributed more or less uniformly throughout the carrier (see for example U.S. Pat. Nos. 3,275,680, 3,743,607 and 3,950,400 and GB 1333449). This was subsequently recognized to be a disadvantage since it was found that the material within the inner part of the carrier did not contribute to the reaction since the reactants did not diffuse significantly into the carrier before reaction occurred. In other words, a significant amount of the palladium and gold never came into contact with the reactants.

In order to overcome this problem, new methods of catalyst manufacture were devised with the aim of producing catalysts in which the active components were concentrated in the outermost shell of the support (shell impregnated catalysts). For example, GB Patent No.1500167 claims catalysts in which at least 90% of the palladium and gold is distributed in that part of the carrier particle which is not more than 30% of the particle radius from the surface. GB Patent No. 1283737 teaches that the degree of penetration into the porous carrier can be controlled by pretreating the porous carrier with an alkaline solution of, for example, sodium carbonate or sodium hydroxide.

Another approach which has been found to produce particularly active catalysts is described in U.S. Pat. No. 4,048,096. In this patent shell impregnated catalysts are produced by a process comprising the steps of (1) impregnating a carrier with aqueous solutions of water-soluble palladium and gold compounds, the total volume of the solutions being 95 to 100% of the absorptive capacity of the catalyst support, (2) precipitating water-insoluble palladium and gold compounds on the carrier by soaking the impregnated carrier in a solution of an alkali metal silicate, the amount of alkali metal silicate being such that, after the alkali metal silicate has been in contact with the carrier for 12 to 24 hours, the pH of the solution is from 6.5 to 9.5; (3) converting the water-soluble palladium and gold compounds into palladium and gold metal by treatment with a reducing agent; (4) washing with water; (5) contacting the catalyst with alkali metal acetate and (6) drying the catalyst. Using this method, catalysts having a specific activity of at least 83 grams of vinyl acetate per gram of precious metal per hour measured at 150° C. can allegedly be obtained. Shell impregnated catalyst are also disclosed in U.S. Pat. No. 4,087,622. Finally, U.S. Pat. No. 5,185,308 also discloses shell impregnated Pd-Au catalyst and the process of manufacture. Each of the above patents is primarily concerned with the manufacture of fixed bed catalyst useful in the manufacture of vinyl acetate.

It would be economically beneficial if the oxacylation of olefins or diolefins, in particular the manufacture of vinyl acetate from ethylene, acetic acid and oxygen could be performed in a fluid bed process. However, until the discovery of the process of the present invention, the preparation of Pd-Au-alkali metal catalyst in fluid bed form has not led to a catalyst having the necessary properties which can lead to an economically viable fluid bed process for the manufacture of vinyl acetate.

SUMMARY OF THE INVENTION

It is the primary object of the present invention to provide a process for the manufacture of a fluid bed Pd based catalyst used in the oxacylation of olefins or diolefins.

It is another object of the present invention to provide a process of manufacturing of a fluid bed Pd based or Pd-Au-K catalyst used in the manufacture of vinyl acetate.

Additional objects and advantages of the invention will be set forth in part in the description which follows and in part will be obvious from the description or may be learned by practice of the invention. The objects and advantages of the invention may be realized and attained by means of the instrumentalities and combinations particularly pointed out in the appended claims.

To achieve the foregoing objects of the present invention, the process for manufacture of a fluid bed catalyst having the following formula: Pd-M-A wherein M comprises Au, Cd, Bi, Cu, Mn, Fe, Co, Ce, U and mixtures thereof, A comprises an alkali metal or mixtures thereof (preferably K) used in the oxacylation of olefins or diolefins, in particular the manufacture of vinyl acetate from ethylene acetic acid and oxygen, comprises milling a fixed bed oxacylation (e.g. vinyl acetate) catalyst precursor comprising Pd-M on a fixed bed support with a fluid bed catalyst aqueous binder material to form a uniform aqueous slurry, spray drying the aqueous slurry to remove the water to form microspheroidal particles of solid fluid bed catalyst precursor, impregnating the microspheroidal particles with a solution of an alkali metal salt to form the fluid bed catalyst. Typically, the weight percent of Pd and alkali in the catalyst are: 0.1 to 5.0 wt % Pd, preferably 0.5 to 2.0 wt %; and alkali greater than 0 to about 10 wt %, preferably 0.01 to 5 wt %. Typically the weight percent of M may range from 0 to about 5%, preferably greater than 0 to 5%, especially preferred being 0.1 to 3%. The balance of the catalyst comprises the inert support material. Depending upon the particular fixed bed catalyst precursor used, the alkali metal acetate may already be present and the need for additional alkali metal salt impregnation after spray drying in some cases may be minimal or non-existent.

Also the need for catalyst to be highly attrition resistant for economical use in fluid bed, will generally require that the catalyst undergo a calcination step at some stage of its preparation. In general it is advantageous for this calcination to occur after the catalyst is spray dried and before the alkali metal salt is added, but with certain fixed bed catalyst precursors the calcination step may be applied after addition of alkali metal salt. After catalyst calcination, a final chemical reduction step may be advantageous. The Pd and other reducible metals present can be reduced with either liquid or gaseous reducing agents as known to those skilled in the art.

A preferred embodiment of the process of the present invention comprises impregnating a fixed bed support material (e.g. silica, zirconia, alumina or mixture thereof) with a metal salt solution of Pd and Au, reducing the metal salts to form metallic Pd and Au on the surface of the support and drying the impregnated support to form the fixed bed catalyst precursor.

In another preferred embodiment of the present invention the drying of the aqueous slurry is performed by spray drying the catalyst slurry at an elevated temperature to form microspheroidal particles of catalyst.

In another preferred embodiment of the present invention a metal salt solution of Au and Pd is prepared to provide a weight ratio of Au to Pd on said resulting catalyst of between 0.10 to 1.00, more preferably 0.2 to 0.8 and especially preferred being 0.25 to 0.75. The specific details of preparation of the salt solutions is conventional and well within the skill of one having ordinary skill in the art. See, for example, U.S. Pat. No. 5,185,308 herein incorporated by reference.

In a preferred embodiment of this aspect of the present invention the alkali metal is selected to be potassium.

DETAILED DESCRIPTION OF THE INVENTION

Reference will now be made in detail to the present preferred embodiments of the invention of which the following examples are set forth for illustrative purposes only.

It has been demonstrated that Pd/Au/K fluid bed catalyst can be obtained by employing the novel procedure set forth below. The procedure comprises impregnating fixed bed support material, in general having a particle size equal to or greater than at least 0.5 mm, preferable at least 3 mm, with an aqueous metal salt solution of Pd and Au, reducing the metal salts to deposit Au and Pd on the support material, drying the support material to form a fixed bed catalyst precursor, milling the fixed bed catalyst precursor with an inert fluid bed aqueous binder to form a uniform aqueous slurry, drying the slurry to remove the water to form microspheroidal particles of catalyst precursor, calcining the dried catalyst and impregnating the spray dried material with a solution of a metal salt of an alkali metal.

Preferably, an aqueous salt solution of Pd and Au are utilized, most preferably an aqueous solution of sodium tetrachloropalladate and chloroauric acid.

A variety of reducing agents may be utilized to precipitate the Pd and Au on the support surface. Typically the precipitation is performed with sodium silicate followed by reduction with hydrazine hydrate.

Size reduction of the dried particles is performed by conventional means such as grinding, crushing, milling, etc. Typically, spray drying of the aqueous slurry is the preferred procedure of removing the water from the aqueous slurry. However, other conventional means of drying the particles to form microspheroidal particles is envisioned in the practice of the present invention.

The dried catalyst is preferably calcined at 400° to 850° C. in air for 1 to 24 hours. Most preferably calcination is between 600° to 700° C. in air for about 1 to 6 hours.

Preferably, an aqueous solution of the metal salt of an alkali metal is utilized. The preferred alkali metal is potassium and an aqueous solution of potassium acetate is typically utilized to impregnate the spray dried particles although other alkali carboxylic salts may be utilized.

In the practice of the present invention suitable fluid bed support/binder materials include silica, alumina, zirconia, and titania among others and mixtures thereof. In general, aqueous sols of these materials are preferred, but fine solid particles which can serve as binders when suspended in liquid medium other than water, for example alcohols such as ethanol, butanol, iso-butanol, are also applicable. Typically 90% of catalyst particles exiting the spray dryer are less than 200 microns in diameter. Preferably 80% of catalyst particles exiting the spray dryer are less than 100 microns in diameter.

Fluid bed catalysts, prepared by this procedure have been demonstrated as very effective for the production of vinyl acetate by reacting ethylene, oxygen, nitrogen and/or $CO_2$ and acetic acid. Typical feed ratios are between 0.05–0.4 $O_2$:0.2–0.7 $N_2/CO_2$:1.0 $C_2H_4$:0.05–0.5 $CH_3COOH$, preferably 0.08–0.35 $O_2$:0.25–0.65 $N_2$:1.0 $C_2H_4$:0.07–0.35 $CH_3COOH$, especially preferred being 0.1–0.3 $O_2$:0.3–0.6 $N_2$:1.0 $C_2H_4$:0.1–0.3 $CH_3COOH$.

The following examples are illustrative of our invention.

Example 1

Preparation of Fixed Bed Catalyst as Reported in U.S. Pat. No. 5,185,308

A representative fixed bed catalyst of composition 0.91 wt % Pd, 0.34 wt % Au, and 3.2 wt % K on KA-160 silica spheres (5 mm) was prepared as follows:

The appropriate weights of $Na_2PdCl_4$ and $HAuCl_4$ were dissolved in 8.7 ml distilled water and impregnated on 15 g KA-160 silica spheres. The wet solid was allowed to sit undisturbed for several hours. An aqueous solution of sodium metasilicate was then poured onto the wet solid. Again the solid was left undisturbed overnight. An aqueous solution of hydrazine hydrate was then added to the solution covering the catalyst spheres. The wet solid was left undisturbed overnight. The solid was then drained and washed free of chloride with distilled water. The solid was dried at 60° C., the appropriate amount of potassium acetate in aqueous solution was then impregnated upon the solid and the finished catalyst was dried at 60° C.

Evaluation of this catalyst under the following conditions:

| Feed: | $C_2H_4$:HOAc:$O_2$:He = 53.1:10.4:7.7:28.6 |
|---|---|
| GHSV: | 3850/hr |
| Temp: | 150° C. (at hot spot) |
| Pressure: | 115 psig |
| Catalyst Charge: | 2.50 g |
| Catalyst Dilution: | 30 cc of 4 mm glass beads | produced 94.2% selectivity to vinyl acetate at 8.0% ethylene conversion (calculation based on the reported oxygen conversion of 32.2%).

Example 2

Preparation of Fluid Bed Catalyst by the Same Technique as Example 1

An attempt to prepare a fluid bed catalyst by the same method of Example 1 except using a microspheroidal silica support in place of KA-160 was carried out. Inspection of the finished catalyst under a microscope indicated the presence of reduced metal particles mixed with the support as well as "clumps" of agglomerated metal and support. Analysis of the catalyst indicated only 0.16 wt % Pd and 0.072 wt % Au, indicating that most of the metal had been washed away.

Evaluation of 5.0 grams of the catalyst under the conditions of Example 1 yielded only 0.56% ethylene conversion with 86% selectivity to vinyl acetate.

Example 3

Preparation of Fluid Bed Catalyst by the Technique of the Present Invention

A catalyst with targeted composition corresponding to 0.90 wt % Pd, 0.40 wt % Au, 3.1 wt % K was prepared by the preferred method using the steps indicated above.

The $Na_2PdCl_4$ (8.57 g) and $HAuCl_4$ (2.18 g) were dissolved in 128 g of distilled water. This solution was then slowly added to 210 g of the spherical silica support (KA-160, Sud Chemie). The solution support mixture was swirled and gently shaken to insure even coverage. This mixture was allowed to sit for two hours at room temperature and essentially all the solution was absorbed into the support. A solution of 15.1 g of sodium metasilicate dissolved in 252 g of distilled water was poured onto the impregnated support. This mixture was allowed to sit for three hours. At this time 26.8 g of hydrazine hydrate was added and the mixture was permitted to sit overnight. The solid spheres were then washed thoroughly with distilled water to remove chloride from the solid. The solid was dried at 60° C. overnight, then the dried solid spheres were crushed. The crushed catalyst (200 g) was milled overnight with 133.3 g of silica sol (30 wt % $SiO_2$) and sufficient water to provide a millable consistency. The catalyst slurry was then spray dried to form microspheroidal particles. A portion of the microspheroidal solid (15 g) was then impregnated with 0.75 g of potassium acetate dissolved in 10 g of distilled water. This solid was dried at 60° C. overnight. Microscopic examination of the finished catalyst indicated well-formed microspheroidal particles.

Evaluation of the catalyst was carried out in a 40 cc fluid bed reactor under the conditions specified in Example 1 except the catalyst bed was composed of 7.5 grams catalyst diluted with sufficient inert silica fluid bed support to produce a total bed volume of 30 cc. An ethylene conversion of 5.2% with 93.7% selectivity to vinyl acetate was obtained, indicating that the preparation method employed was effective.

Examples 4–8

Effect of Process Variables on Fluid Bed Catalyst Performance

The catalyst prepared in Example 3 was tested in order to determine the effect of oxygen feed concentration, space velocity and temperature on performance. The percent ethylene fed was maintained constant and nitrogen fed was adjusted downward as oxygen or acetic acid levels increased. The following observations were noted:

TABLE I

| Example | 4 | 5 | 6 | 7 | 8 |
|---|---|---|---|---|---|
| % $O_2$ Fed | 7.7 | 15.4 | 15.4 | 15.4 | 15.4 |
| % $HOA_C$ Fed | 10.4 | 10.4 | 15.8 | 10.4 | 10.4 |
| T (deg-C.) | 160 | 160 | 160 | 160 | 170 |
| GHSV | 3080 | 3850 | 3850 | 3080 | 3080 |
| C2 = Conversion (%) | 6.0 | 7.4 | 7.7 | 8.5 | 10.2 |
| VAM Selectivity (%) | 93.0 | 90.6 | 92.5 | 91.2 | 86.4 |

Table I set forth above shows that good selectivity and conversion are maintained over a wide range of feed conditions.

Example 9

Dissolved 6.80 g of $Na_2PdCl_4$ and 1.73 g of $HAuCl_4$ in 110 g of distilled $H_2O$ and impregnated this solution on 200 g of KA-160 silica spheres (5 mm). Allowed wet solid to sit for two hours then added a solution of 12.0 g of $Na_2SiO_3$ in 240 g of distilled $H_2O$, mixed gently and allowed solid to sit undisturbed for 2 hours. To this mixture was added 21.3 g of 55% hydrazine hydrate. This mixture was allowed to sit overnight. Drained solution from solid and washed solid with fresh distilled $H_2O$ until negative test for chloride was obtained. The catalyst precursor spheres were then dried overnight at 60° C. 200 g of this catalyst precursor were crushed and mixed with 19.05 g crushed KA-160 (washed to remove Cl), 202.8 g of Snotex-N-30 silica sol (36 wt % solids), and sufficient water to provide a millable consistency to the slurry. This slurry was milled overnight, then spray dried. The microspheroidal catalyst particles were oven dried at 110° C. Elemental analysis of this solid found 0.62 wt % Pd and 0.23 wt % Au.

Dissolved 1.66 g of potassium acetate in 13.5 g of distilled $H_2O$ and impregnated this solution of 15.85 g of the above microspheroidal particles. After drying the solid contained 9.5 wt % potassium acetate.

Examples 10 through 13

A mixture of 14.5 g of the catalyst in Example 9 and sufficient fluidizable silica to provide 30 cc were placed in the fluid bed test reactor. The conditions and results are as follow:

| Example | 10 | 11 | 12 | 13 |
|---|---|---|---|---|
| % $C_2H_4$ fed | 50.2 | 48.4 | 45.6 | 45.9 |
| % $O_2$ fed | 5.3 | 8.6 | 9.7 | 8.9 |
| % HOAc fed | 10.3 | 9.9 | 13.5 | 13.7 |
| % $N_2$ fed | 34.3 | 33.1 | 31.2 | 31.4 |
| Total Flow | 380.8 | 394.3 | 418.5 | 415.9 |
| Temp (C.) | 156 | 157 | 165 | 158 |
| Pressure (psig) | 115 | 115 | 115 | 115 |
| $C_2H_4$ conversion (%) | 12.9 | 17.5 | 20.5 | 16.2 |
| VAM selectivity (%) | 90.0 | 87.7 | 86.1 | 89.3 |

Example 14

A portion of the catalyst prepared in Example 9 was calcined at 640° C. in air for 2 hours. This sample was reduced in 21% $H_2$ in $N_2$ stream, starting at room temperature and ramping the temperature gradually to 100° C. This temperature was held for 3 hours then the catalyst was cooled under $N_2$. This sample was evaluated for attrition resistance and found to be sufficiently attrition resistant for commercial use.

Example 15

A 16.0 g portion of the catalyst prepared in Example 9 was calcined at 640° C. in air for 2 hours. To this calcined solid was added 1.6 g of potassium acetate dissolved in 13.5 g $H_2O$. The catalyst was then dried at 60° C.

Examples 16 through 17

16.05 g of the catalyst of Example 15 was mixed with sufficient inert microspheroidal silica to give 33 cc. This catalyst mixture was tested in a fluid bed reactor with the following results.

| Example | 16 | 17 |
|---|---|---|
| % $C_2H_4$ fed | 47.2 | 45.2 |
| % $O_2$ fed | 6.7 | 10.5 |
| % HOAc fed | 14.0 | 13.4 |
| % $N_2$ fed | 32.2 | 30.9 |
| Total Flow | 405 | 422.5 |
| Temp (C.) | 154 | 168 |
| Pressure (psig) | 115 | 115 |
| $C_2H_4$ conversion (%) | 11.1 | 16.9 |
| VAM selectivity (%) | 91.8 | 83.7 |

Example 18

A spray dried catalyst was prepared in the manner described in Example 9 except that it contained 17 wt % silica from the sol and levels of palladium and gold reagents were increased to give 0.69 wt % Pd and 0.25 wt % Au (no potassium acetate). 16 g of this microspheroidal solid was calcined 0.5 hours at 400° C. followed by 2 hours at 640° C. 1.57 g of potassium acetate dissolved in 13.5 g of distilled $H_2O$ was impregnated upon 15.0 g of the calcined solid. This final catalyst was dried at 60° C.

Examples 19 through 21

13.3 g of the catalyst of Example 18 was mixed with sufficient inert microspheroidal silica to give 30 cc. This catalyst mixture was tested in a fluid bed reactor with the following results.

| Example | 19 | 20 | 21 |
|---|---|---|---|
| % $C_2H_4$ fed | 47.9 | 45.6 | 44.8 |
| % $O_2$ fed | 5.1 | 9.7 | 11.1 |
| % HOAc fed | 14.2 | 13.6 | 13.4 |
| % $N_2$ fed | 32.7 | 31.0 | 30.6 |
| Total Flow | 399 | 419 | 426 |
| Temp (C.) | 151 | 158 | 167 |
| Pressure (psig) | 115 | 115 | 115 |
| $C_2H_4$ conversion (%) | 11.5 | 15.5 | 18.7 |
| VAM selectivity (%) | 92.0 | 89.3 | 86.0 |

Example 22

Other fixed bed vinyl acetate catalysts which contain the metals distributed essentially throughout the support particle may also be used as the fixed bed precursor of the present invention. For example the Pd/Au containing catalysts described in U.S. Pat. No. 3,743,607 may be advantageously used. A representative preparation of such a catalyst follows:

1 kg of silica support (3 mm) is impregnated with an aqueous solution of 10 g of Pd in the form of $PdCl_2$ and 0.4 g Au in the form of $HAuCl_4$. The thoroughly dried solid is then placed in a solution of 3% hydrazine hydrate at 40° C. After the reduction of the Pd and Au is complete the solid is washed to remove chloride. After drying the catalyst precursor can then be crushed, and milled in the presence of silica sol (sufficient sol to provide ~20 wt % silica from the sol). Additional water is added until the slurry is of the appropriate viscosity for efficient milling. The milling is continued overnight, then the milled slurry is spray dried to produce microspheroidal catalyst particles which are suitable for use in a fluid bed reactor. Impregnation of these microspheroidal particles with ~7.0 wt % potassium acetate results in fluid bed catalyst which is both active and selective for the oxidation of ethylene plus acetic acid to vinyl acetate.

Example 23

A catalyst containing palladium acetate, cadmium acetate, and potassium acetate is prepared according to the teachings of U.S. Pat. No. 3,759,839. The appropriate amounts of these three reagents are dissolved in acetic acid (sufficient to fill the pore volume of the support) and deposited on silica spheres (5 mm) to give, upon drying, the following composition: 1.5 wt % palladium acetate, 4.5 wt % cadmium acetate, and 4.5 wt % potassium acetate. This fixed bed catalyst can then be used as a precursor in the preparation of a fluid bed vinyl acetate catalyst. The spheres of the fixed bed catalyst are crushed, then ball milled with the appropriate amount of silica sol (Nisson Snotex-N-30) to result in ~17% silica from sol in the spray dried catalyst. Sufficient water is also added to the slurry to provide a fluid consistency. After sufficient milling (usually overnight is adequate) the slurry can be spray dried to form microspheroidal, fluidizable catalyst particles. This fluidizable catalyst can then be calcined, and reduced with either gaseous reducing agents (such as $H_2$ or ethylene) or liquid reducing agents (such as aqueous; hydrazine), or reduced in situ. When tested in the fluid bed reactor under the conditions described in Example 3, good yields of vinyl acetate are obtained.

While the invention has been described in conjunction with specific embodiments, it is evident that many alterations, modifications and variations will be apparent to those skilled in the art in light of the foregoing description. Accordingly, it is intended to embrace all such alternatives, modifications and variations as fall within the spirit and broad scope of the appended claims.

What we claim is:

1. A method for the preparation of fluidizable catalyst having the formula Pd-M-A where M is selected from the group consisting of Au, Cd, Bi, Cu, Mn, Fe, Co, Ce, U and mixtures thereof, A is selected from the group consisting of an alkali metal and mixtures thereof and M is present in a range of from 0 to about 5 wt % and A is present in a range of greater than 0 to 10 wt % which is useful in the oxacylation of olefins and diolefins in a fluid bed reactor comprising:

a) preparing a fixed bed catalyst precursor consisting primarily of Pd-M supported on a fixed bed catalyst support, b) milling the fixed bed catalyst precursor with a fluid bed catalyst binder to form a slurry, c) drying the slurry to form microspheroidal particles of solid fluid bed catalyst precursor, d) calcining the dried solid fluid bed catalyst precursor, and e) impregnating the microspheroidal particles of fluid bed catalyst precursor with a solution of an alkali metal salt to produce a fluid bed catalyst.

2. The method of claim 1 wherein M equals Au.

3. The method of claim 2 in which the fixed bed catalyst precursor consists of a support with a surface layer of palladium-gold alloy.

4. The method of claim 3 in which the fixed bed catalyst surface layer of Pd-Au alloy extends substantially uniformly to a depth less than 0.5 mm from the surface of the fixed bed catalyst support.

5. The method of claim 1 in which the fluid bed catalyst binder is an aqueous slurry of an inert support selected from the group consisting of silica, alumina, zirconia, titania and mixtures thereof.

6. The method of claim 1 in which the milled slurry of fixed bed catalyst precursor and fluid bed catalyst binder is dried under conditions such that 90% of the microspheroidal catalyst particles exiting the dryer are less than 200 microns in diameter.

7. The method of claim 1 in which the milled slurry of fixed bed catalyst precursor and fluid bed binder is dried under conditions such that 80% of the microspheroidal catalyst particles exiting the dryer are less than 100 microns in diameter.

8. The method of any one of claims 1 to 7 wherein the calcination is performed in air at 400°–900° C. for 1 to 24 hours.

9. The method of claim 8 wherein the calcination is performed in air at 550°–700° C. for 1 to 6 hours.

10. The method of claim 8 wherein the calcined microspheroidal particles are treated with a reducing agent prior to impregnation with alkali metal salt.

11. The method of claim 1 wherein the alkali metal salt is selected from the group consisting of sodium acetate, potassium acetate, and lithium acetate.

12. The method of claim 1 wherein the fixed bed catalyst precursor is impregnated with the solution of alkali metal salt prior to milling with the fluid bed catalyst binder.

13. A method for the preparation of a fluid bed vinyl acetate catalyst having the formula Pd-M-A where M is selected from the group consisting of Au, Cd, Bi, Cu, Mn, Fe, Co, Ce, U and mixtures thereof, A is selected from the group consisting of an alkali metal and mixtures thereof and M is present in a range of from 0 to about 5 wt % and A is present in a range of greater than 0 to 10 wt % comprising:

a) preparing a fixed bed catalyst precursor consisting primarily of Pd-M supported on a fixed bed catalyst support, b) milling the fixed bed catalyst precursor with a fluid bed catalyst binder to form a slurry, c) drying the slurry to form microspheroidal particles of solid fluid bed catalyst precursor, d) calcining the dried solid fluid bed catalyst precursor, and e) impregnating the microspheroidal particles of fluid bed catalyst precursor with a solution of an alkali metal salt to produce a fluid bed catalyst.

14. The method of claim 13 wherein M equals Au.

15. The method of claim 14 wherein A equals K.

\* \* \* \* \*